United States Patent [19]

Turnas

[11] 4,052,883
[45] Oct. 11, 1977

[54] STATIC FREE MAGNETIC HOLDING AND RELEASE MEANS

[75] Inventor: Angelo Turnas, St. Clair Shores, Mich.

[73] Assignee: Ring Tool and Die Company, Detroit, Mich.

[21] Appl. No.: 731,228

[22] Filed: Oct. 12, 1976

[51] Int. Cl.² .............................................. G01N 3/30
[52] U.S. Cl. ........................................................ 73/12
[58] Field of Search ................ 73/11, 12, 1 D, 133 R; 335/285, 295; 292/251.5

[56] References Cited

U.S. PATENT DOCUMENTS

| | | | |
|---|---|---|---|
| 2,243,616 | 5/1941 | Bing et al. | 335/295 |
| 2,662,392 | 12/1953 | Sullivan | 73/12 |
| 2,740,286 | 4/1956 | DeVost et al. | 73/12 |
| 2,953,030 | 9/1960 | Replogle et al. | 73/12 X |
| 3,452,310 | 6/1969 | Israelson | 335/295 X |

OTHER PUBLICATIONS

R. W. Armstrong – "NBS Dynamic Seat Belt Tester" –Proc. 10th Stapp Car Crash Conf., 6571st, Aeromedical Research Lab., Alamogordo, N. Mex., Nov. 8–9, 1966, pp. 38–45.

Primary Examiner—Charles A. Ruehl
Attorney, Agent, or Firm—Robert G. Mentag

[57] ABSTRACT

A static free permanent magnet holding and release means for use in various machines, such as a seat belt testing machine. The permanent magnet means is operable between an energized condition and a deenergized condition. A preloaded holding means is movable to a first position in engagement with said permanent magnet means for a holding engagement with the permanent magnet means when it is in an energized condition, and movable to a second position by the preload thereon when the permanent magnet means is in a de-energized position for releasing the holding means.

8 Claims, 4 Drawing Figures

4,052,883

STATIC FREE MAGNETIC HOLDING AND RELEASE MEANS

BACKGROUND OF THE INVENTION

1. Field of the Invention

This invention relates generally to holding and release means for use in various machines which perform various types of operations, such as testing machines for testing automobile safety seat belts, and the like. The invention is particularly concerned with a static free magnetic holding and release means which functions to hold a movable slide member in a first position and then releases the movable slide member to permit it to be moved to a second position by a pre-load or biasing means without any hesitation in the releasing action, and without any injurious drag or friction which might produce vibrations and other unwanted effects in the machine in which the holding and release means is being used, as for example in the apparatuses employed with the machine for taking various readings, such as oscilloscope readings in automobile safety seat belt testing machines.

2. Description of the Prior Art

It is known in the testing machine art to provide machines for testing automobile safety seat belts wherein the free end of the seat belt is releasably secured and the seat belt retractor is mounted on a movable slide member which is held in a first position by a holding and release means and then moved to a second position by a pre-load or biasing means when the movable slide member is released. The disadvantage of the prior art holding and release means employed in such seat belt testing machines is that they employed mechanical release means which provide a drag or friction, which creates vibrations that injuriously affect the readings on various testing apparatuses employed with the seat belt testing machines, as for example, readings on an oscilloscope. A further disadvantage of the prior art mechanical release means is that the friction produced by the release action of the mechanical means produces not only vibrations but sounds which also affect the readings of instruments employed with a seat belt testing machine.

SUMMARY OF THE INVENTION

In accordance with the present invention, the holding and release means is a static free magnetic holding and release means which employs a permanent magnet. The seat belt testing machine with which the static free magnetic holding and release means of the present invention is illustrated comprises a stationary table or base on which is slidably mounted a slide plate that carries a fixture for holding an automobile safety seat belt retractor. The machine includes a releasable locking means for holding the free end of the seat belt in a fixed position so that the belt is held in a stretched out position that simulates the use position in an automobile. The movable slide plate carrying the seat belt retractor is adapted to be moved into a first position by a suitable fluid cylinder and to be held in that first position by the static free magnetic holding and release means of the present invention. A suitable pre-load or biasing means, such as an elastic surgical tubing biasing means, is employed for moving the movable slide plate to a second retracted position for exerting a test pull on the seat belt when the static free magnetic holding and release means of the present invention is operated to release the movable slide plate.

The static free magnetic holding and release means of the present invention overcomes the aforedescribed advantages of the prior art mechanical holding and release means for use in seat belt testing machines and the like, in that it operates without any hesitation and without any friction or drag during a release operation. The permanent magnet holding and release means of the present invention is static free and it does not produce any electromagnetic flux fields which would emanate from an electromagnetic holding means, and which would upset the readings of test instruments such as an oscilloscope being employed with the seat belt testing machine.

Other objects, features and advantages of this invention will be apparent from the following detailed description, appended claims, and the accompanying drawings.

DESCRIPTION OF THE PREFERRED EMBODIMENT

Figure 1:
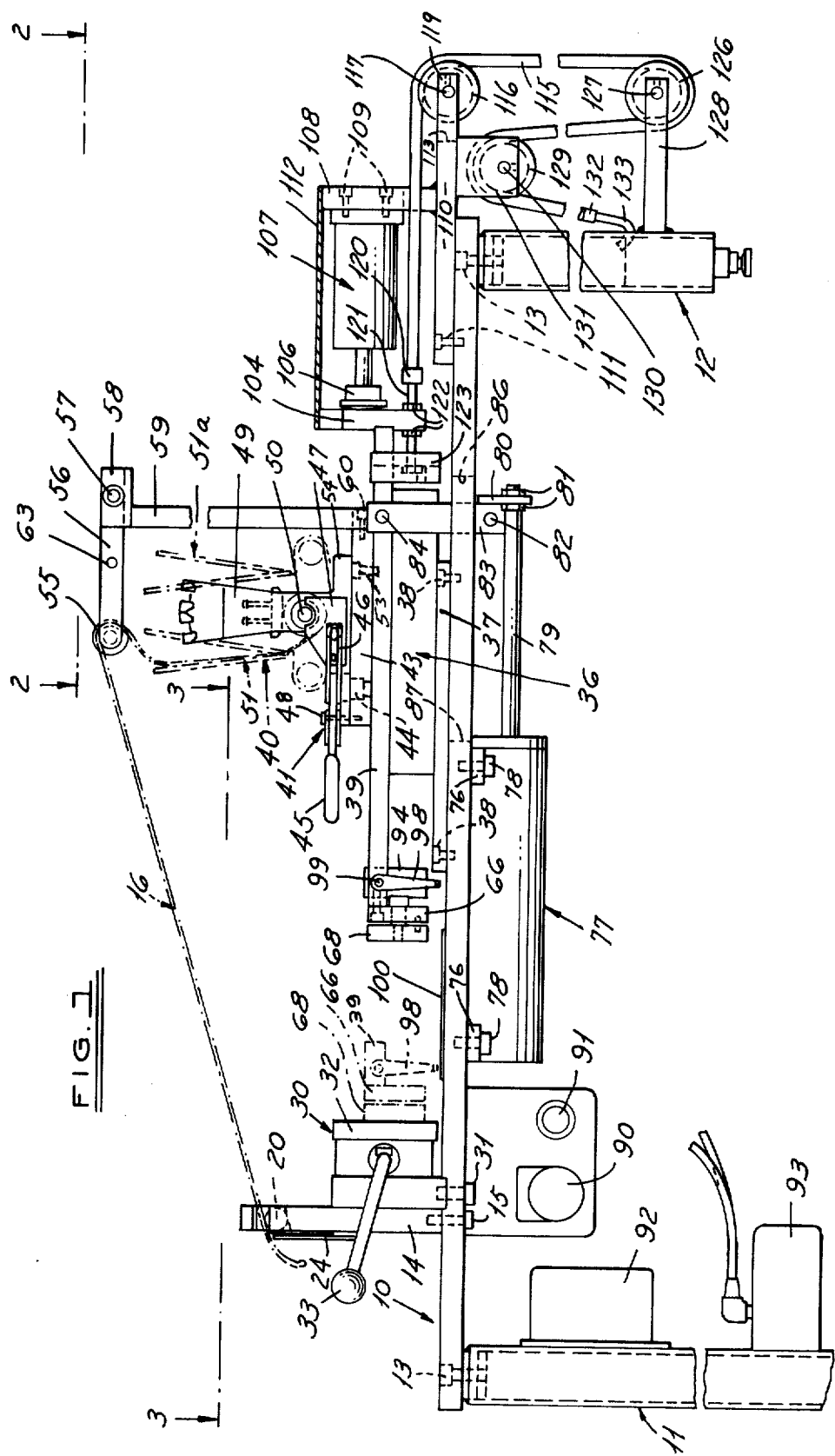
FIG. 1 is a broken, side elevation view of an automobile safety seat belt testing machine in which is employed an embodiment of the static free magnetic holding and release means of the present invention.

Referring now to the drawings, and in particular to FIG. 1, the numeral 10 generally designates a table or base of an automobile safety seat belt testing machine. The machine table 10 is supported at the front and rear ends thereof by suitable ground engaging support legs, generally indicated by the numerals 11 and 12, respectively. The support legs 11 and 12 may be of any suitable type, as for example they may be rectangular and tubular in cross section. The support legs 11 and 12 are secured to the work table by any suitable means, as by the machine screw 13.

Figure 4:
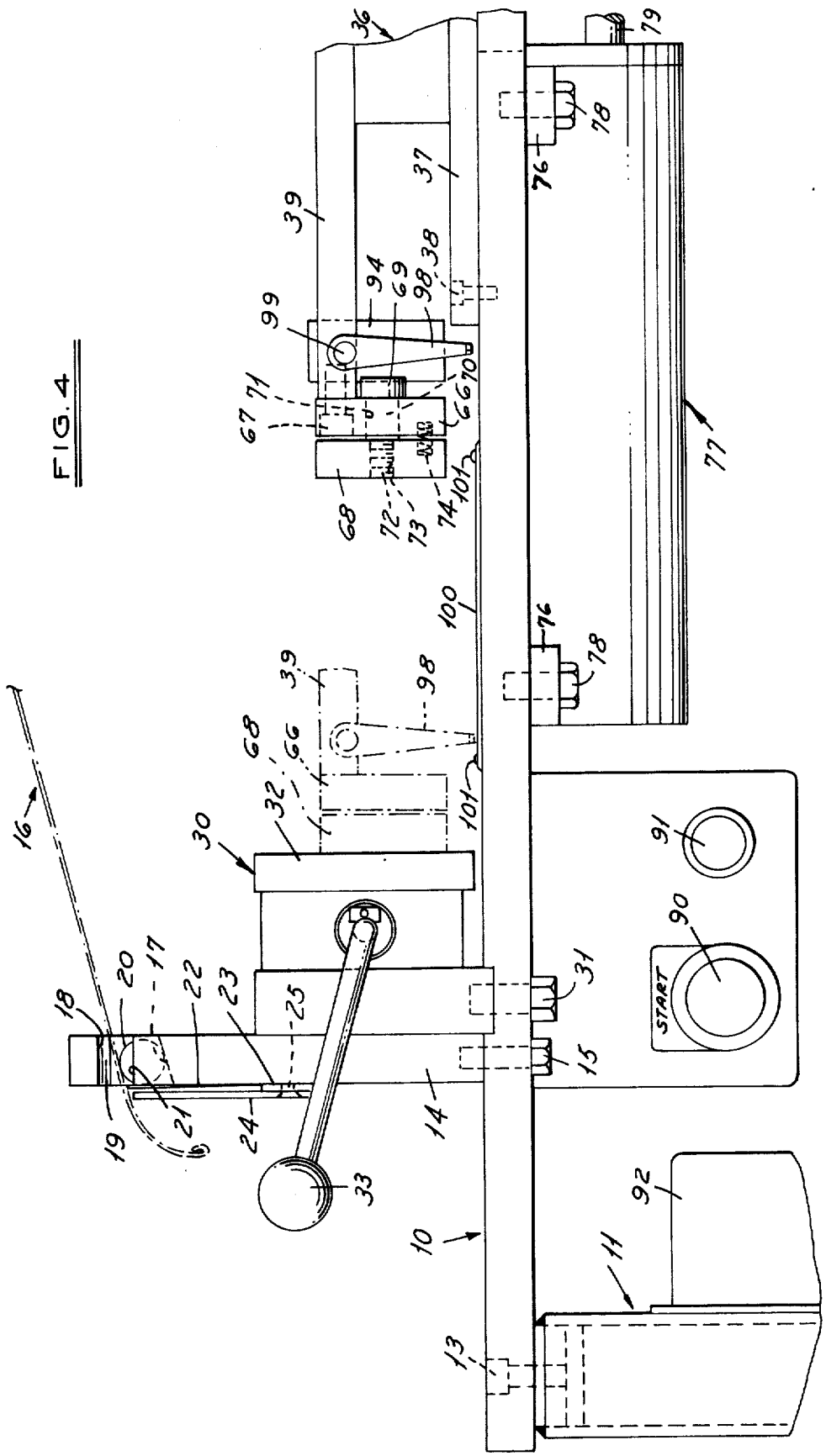
FIG. 4 is a front elevation view of the structure illustrated in FIG. 3 taken along the line 4—4 thereof, and looking in the direction of the arrows.

As best seen in FIG. 4, a vertically extended plate 14 is fixedly secured by any suitable means, as by machine screws 15, to the machine table 10, at the left end thereof as viewed in FIGS. 1 and 4. The vertical plate 14 has a seat belt releasable retainer means formed in the upper end thereof, and it generally comprises a knurled check roller pin 20 mounted in a transverse slot, as described in detail hereinafter. The numeral 16 generally indicates a conventional automobile safety seat belt, and in FIG. 4, the free end thereof is shown as being mounted through said opening formed through the upper end of the vertical plate 14, and being held in a releasable position by the check roller pin 20.

The numeral 17 designates the lower sloping end of the opening through the plate 14. Numeral 18 designates the upper end of said opening. Numeral 19 designates the sloping side end of the opening which limits the upward movement of the roller pin 20. The roller pin 20 cannot be moved forward, or to the right as viewed in FIG. 4, out of the opening since it is of a diameter that is larger than the distance between the front edge of the sloping end of the opening 17 and the lower edge of the outwardly sloping side edge 19. The check roller pin 20 is retained in the opening by a vertical band spring 22. The opening through the upper end of the plate 14 has a side opening which extends between a lower line designated by the numeral 21 and the upper end 18 of the opening so that the free end of the seat belt 16 can be slid sidewardly into the opening over the check roller pin 20. The check roller pin 20 is inserted into said opening from the rear end or left side thereof, as viewed in FIG. 4, and it is retained therein by the band spring 22. The band spring 22 is secured to the plate 14 by the spacer plate 23 and an elongated plate 24. The plate 24 limits the outward movement of the band spring 22 away from the plate 14.

It will be seen that when a tension is applied on the seat belt 16, which is directed to the right as viewed in FIG. 4, the check roller pin 20 will be moved up the sloping lower end 17 of the opening through the plate 14 so as to move the free end of the seal belt 16 against the tapered sloping side wall portion 19 of said opening to releasably grip the seat belt in a fixed position.

As illustrated in FIGS. 1 and 4, the static free magnetic holding and release means of the present invention, includes a releasable permanent magnet means, generally indicated by the numeral 30, which is mounted on the machine table 10 in a position adjacent the plate 14 and along the front side thereof. The permanent magnet means 30 may be of any suitable type, as for example a permanent magnetic chuck available on the market from the Magna-Tool Corporation of Troy, Mich. Such magnetic chucks are available in various sizes. The magnetic chuck generally illustrated by the numeral 30 includes the front plate 32, and an operating lever 33 for making and breaking the magnetic field created by the chuck 30 when the lever 33 is moved between an operative and inoperative position. The operation of the magnetic chuck 30 is well known to those in the magnetic chuck art. The magnetic chuck 30 may be fixedly secured to the machine table 10 by any suitable means, as by suitable machine screws 31.

As shown in FIG. 1, a ball slide apparatus, generally indicated by the numeral 36, is operatively mounted on the machine table 10 in a position spaced apart and to the right of the permanent magnet means 30. The ball slide 36 may be of any suitable type, as for example the ball slide shown in U.S. Pat. No. 3,113,807. The ball slide 36 is provided with a mounting plate 37 which is fixedly secured to the machine table 10 by any suitable means, as by machine screws 38. The ball slide 36 further includes an upper slidable plate 39 on which is operatively mounted a seat belt retractor holder means generally indicated by the numeral 40. The seat belt retractor holder means 40 may be of any suitable type.

Figure 2:
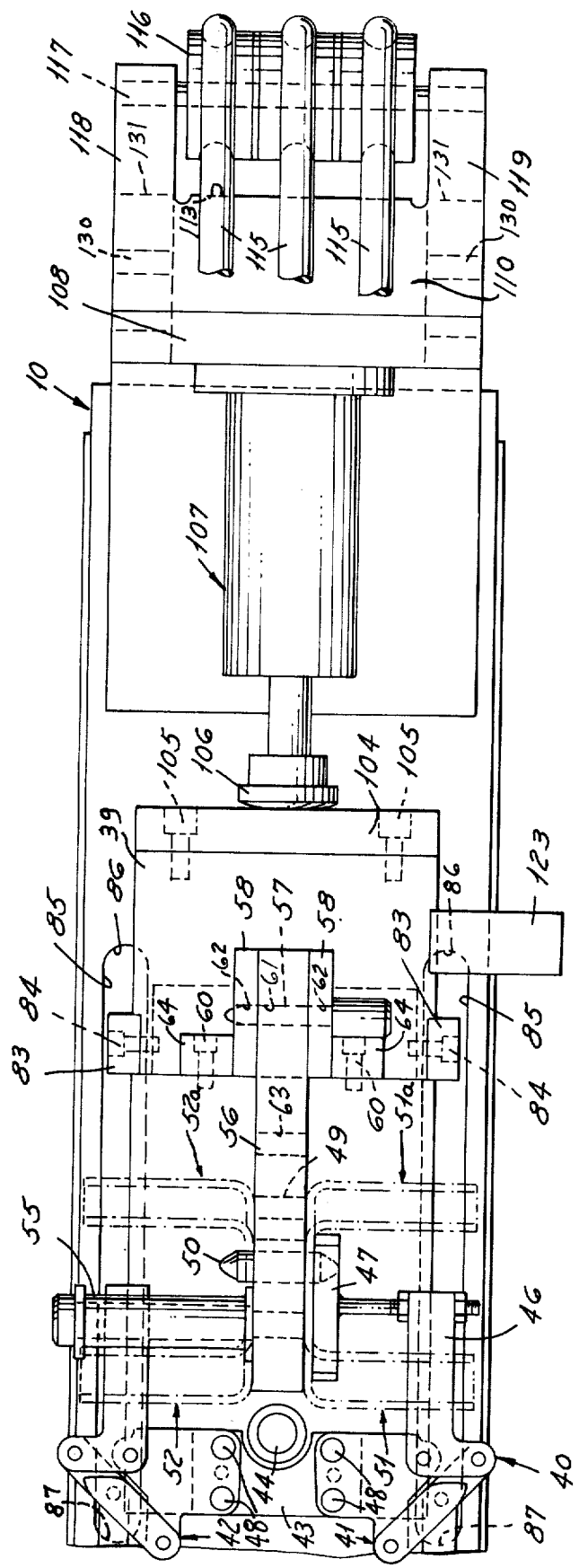
FIG. 2 is an enlarged, partial top plan view of the structure illustrated in FIG. 1, taken along the line 2—2 thereof, and looking in the direction of the arrows.
Figure 3:
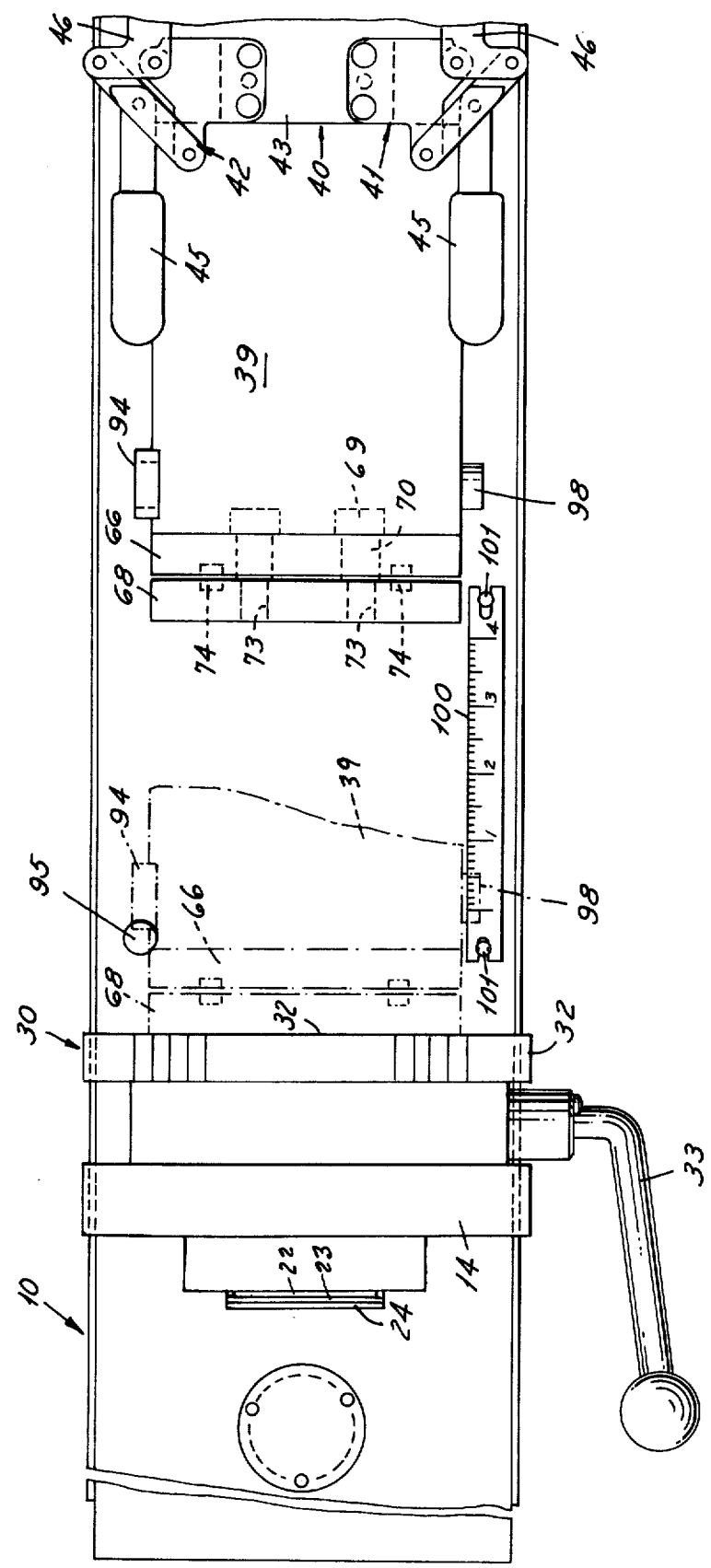
FIG. 3 is an enlarged, partial top plan view of the structure illustrated in FIG. 1, taken along the line 3—3 thereof, and looking in the direction of the arrows.

The seat belt retractor holder means 40 includes a pair of toggle clamps generally indicated by the numerals 41 and 42 in FIGS. 2 and 3. The toggle clamps are conventional clamps and of the type known as "De-Sta-Co" toggle clamps which are available on the market from the De-Sta-Co Division, Dover Corporation, 350 Midland, Highland Park, Mich. The toggle clamps 41 and 42 are operatively secured by suitable machine screws 48 to the upper side of a plate 43. The plate 43 is secured to the slidable plate 39 by any suitable means, as by suitable machine screws 53.

As shown in FIGS. 1 and 2, an upwardly extending center post 49, having a base portion 54, is mounted on top of the plate 43 and it is pivotally secured thereto by a suitable pivot pin 44. The center post 49 carries a horizontal shaft 50 upon which a seat belt retractor is mounted for seat belt test purposes. As illustrated in FIG. 2, a seat belt retractor clamp member 47 is provided for holding a seat belt retractor (not shown) on one end of the shaft 50. The clamp member 47 is operatively carried on a lever 46 of the one toggle clamp 41. As shown in FIGS. 1 and 3, the toggle clamp 41 is provided with an operating handle 45. The other toggle clamp 42 also carries a clamp member as 47 (not shown) for holding a seat belt retractor on the other end of the shaft 50. Accordingly, both right hand and left hand seat belt retractors can be selectively and separately mounted on the shaft 50 for testing the seat belts carried thereon. The numerals 51 and 51a designate broken line outlines of fixtures on one end of the shaft 50 for selectively holding seat belt retractors in positions tilted 8° forward or 8° rearward from the vertical for testing seat belts under such conditions. As shown in FIG. 2, the same type fixtures indicated by the numerals 52 and 52a, are illustrated on the other end of the shaft 40.

As illustrated in FIG. 1, a seat belt 16 being tested by the illustrated machine is directed upward from its respective seat belt retractor and mounting fixture and threaded over a guide roller 55, and thence forward or to the left as viewed in FIG. 1, for retaining engagement with the afore-described check roller 20. The roller 55 is illustrated in FIG. 2 as being disposed for use on one side of the center post 49, but it will be understood that it can be reversed in position for use on the other side of the center post 49. As shown in FIGS. 1 and 2, the roller 55 is operatively mounted on a horizontal carrier arm 56 which has its right end, as viewed in FIGS. 1 and 2, disposed on the top of a support post 59, between two support arms 58 which are fixedly carried on the upper end of the support post 59. The carrier arm 56 is releasably secured to the support arms 58 by a releasable mounting pin 57 which is slidably mounted through the bores 62 formed through the support arms 58 and the transverse bore 61 formed through the rear end of the carrier arm 56. The carrier arm 56 is shown in FIGS. 1 and 2 in a forward position to cooperate with the fixtures 51 and 52 for an 8° forward fixture disposition, as mentioned hereinbefore. The roller may be moved to the right, as viewed in FIGS. 1 and 2, to cooperate with the 8° rearward disposition fixtures 51a and 52a by removing the pin 57 and moving the carrier arm 56 rearwardly to permit the second pin hole 63 to be aligned with the pin holes 62 for retaining the carrier arm 56 in a rearward position. As shown in FIGS. 1 and 2, the support post 59 is provided on the lower end thereof with sidewardly extending mounting arms 64 which are fixedly secured to the plate 43 by suitable machine screws 60.

As best seen in FIGS. 3 and 4, a holding plate means is operatively mounted on the front end of the slidable plate 39 and it includes an inner rectangular aluminum plate 66. The aluminum plate 66 is disposed vertical or transverse to the horizontal plate 39, and it is secured thereto by suitable aluminum screws 67 (FIG. 4). The holding plate means further includes a steel plate 68 which is of the same overall shape and dimension as the aluminum plate 66. The steel plate 68 is disposed adjacent the front face of the aluminum plate 66, and it is attached thereto by a suitable bolt and spring attachment means which permits the steel plate 68 to float, longitudinally of the slidable plate 39, to permit an optimum seating engagement with the front plate 32 of the magnetic holding means 30.

The steel plate 68 is attached to the aluminum plate 66 by a pair of socket head shoulder screws 69 which are each provided with a cylindrical shoulder 70 that is slidably mounted in a mating bore 71 formed through the aluminum plate 66. The threaded end of each of the screws 69 is threadably mounted in a mating threaded bore 73 formed in the steel plate 68. As shown in FIGS. 3 and 4, the steel plate 68 is normally in a spaced apart position forwardly from the aluminum plate 66, and it is biased to said spaced apart position by a plurality of springs 74. In one embodiment of the invention, four springs 74 were used. The springs 74 are each mounted with their inner end in a recess in the front end of the aluminum plate 66 and the outer end disposed in a suitable mating recess in the rear of the steel plate 68. It will be seen that the last mentioned spring and shoulder screw mounting means permits the steel plate 68 to move relative to the aluminum plate 66 a predetermined distance, to permit optimum seating engagement with the holding means plate 32.

As shown in FIGS. 1 and 4, a fluid cylinder, generally indicated by the numeral 77, such as an air cylinder, is fixedly secured to the underside of the machine table 10. The fluid cylinder 77 is provided with legs 76 which are secured by suitable machine screws 78 to the table 10. The fluid cylinder 77 is provided with the usual cylinder rod 79 which has operatively mounted on its outer threaded end a vertically extended drive flange or plate 80 (FIG. 1). The drive plate 80 is secured to the outer end of the cylinder rod 79 by a pair of suitable lock nuts 81. The fluid cylinder 77 is adapted to move the slidable plate 39 from the solid line position shown in FIG. 1 to an advanced position, where the holding means plate 68 is operatively engaged by the magnetic holding means 30, as shown by the broken line position of the plate 68 in FIG. 1.

As best seen in FIG. 2, the slidable plate 39 has fixedly secured on the opposite sides thereof, adjacent the rear end thereof, a pair of downwardly extended drive arms 83 which are secured to the slidable plate 39 by any suitable means, as by suitable machine screws 84. Each of the drive arms 83 extends downwardly through an elongated slot 85 which is formed through the machine table 10 and extends longitudinally thereof. The ends of the slot 85 are indicated by the numerals 86 and 87. The lower ends of the drive arms 83 are interconnected by a suitable drive rod or drive shaft 82 which is adapted to be engaged by the drive flange 80 when the fluid cylinder 77 is operated to draw the cylinder rod 79 inwardly.

Any suitable control circuit may be provided for operating the cylinder 77. The start switch for operating the cylinder 77 is indicated by the numeral 90 in FIG. 1 and an "on" signal light 91 is also shown for indicating that the control system is energized. The numeral 92 in FIG. 1 designates a suitable voltage reducer for operating a four-way AC solenoid operated valve 93 which controls the operation of the cylinder 77. Any suitable valve may be employed for carrying out the operation of the valve 93. A switch operating tab 94 is mounted on one side of the front end of the slidable plate 39 as shown in FIGS. 1 and 3. When the movable slide plate 39 is moved to the left, as viewed in FIGS. 1 and 3, to the broken line position indicated in said Figures, the operating tab 94 engages a switch 95 (FIG. 3) which reverses the action of the valve 93 for reversing the fluid cylinder 77 to bring it back to its start position shown in FIG. 1.

As shown in FIGS. 1 and 4, a pivotally mounted, and freely movable, indicator arm 98 is pivotally secured by a suitable pivot pin 99 to one side of the front end of the movable slide plate 39. The indicator arm 98 is allowed to swing freely, and it extends downwardly into a closely spaced apart relationship with a 4 inch long steel rule 100. As shown in FIG. 3, the steel rule 100 is calibrated in inches, and it is secured to the machine table 10 by screws 101.

As shown in FIGS. 1 and 2, a bumper plate 104 is secured to the rear end of the movable slide plate 39 by suitable machine screws 105 (FIG. 2). As shown in FIG. 1, the bumper plate 104 extends vertically upward and downward relative to the movable slide plate 39, and it is adapted to engage the head 106 of the cylinder rod of a suitable shock absorber 107. The shock absorber 107 is disposed longitudinally of the machine table 10 and it is secured by suitable machine screws 109 to a vertically disposed mounting plate 108. The mounting plate 108 is secured by any suitable means, as by welding, to the top side of an extension plate 110 which is secured to the machine table 10 by suitable machine screws 111. A cover 112 is secured by any suitable means to the top of the mounting plate 108 and it extends forwardly over the shock absorber 107.

As shown in FIG. 2, the extension plate 110 is provided wit a central recess 113 so as to form a pair of rearwardly extended horizontal support arms 118 and 119. A transverse shaft 117 is mounted in the recess 113, and it has its ends operatively supported by the support arms 118 and 119. A nylon roller member 116 is rollably mounted on the shaft 117 by suitable ball bearing means (not shown), and it has mounted therearound, in suitable grooves, three elongated surgical tubing members 115. It will be understood that any other suitable elastomeric or resilient elongated members can be used instead of the surgical tubing 115 for carrying out the hereinafter described function of said tubing members 115.

As shown in FIG. 1, each of the tubing members 115 has its front end attached by a suitable tubing clamp 120 to the threaded end of a bolt 121. Each of the bolts 121 is threadably mounted through the lower end of the bumper plate 104, and it is secured in a suitable adjusted position by a pair of lock nuts 122. As shown in FIGS. 1 and 2, a mounting plate 123 is fixedly secured, as by welding, to the rear end of the movable slide plate 139 for supporting suitable testing instruments, such as an oscilloscope.

As shown in FIG. 1, the surgical tubing members 115 are extended downwardly from the roller 116 and around a second roller member 126 which is also made from nylon and which is mounted by suitable roller bearings (not shown) on a shaft 127 which has its ends operatively mounted between the rear ends of a pair of horizontal support arms 128 which are disposed in vertical alignment with the support arms 118 and 119. The front ends of the support arms 128 are fixedly secured, as by welding, to the rear table leg 12. The surgical tubing members 115 extend upwardly and over a nylon roller 129 and then downwardly. The nylon roller 129 is supported by a suitable ball bearing means (not shown) on a shaft 130 which is supported between a pair of laterally spaced apart mounting plates 131 which have their upper ends fixed, as by welding, to the underside of the extension plate 110 and in a position spaced forwardly from the first two mentioned nylon rollers 116 and 126. The rear ends of the surgical tubing members 115 are each attached by a suitable tubing clamp 132 to a steel pin hook 133 which is hooked to the rear table leg 12 in a suitable manner, as illustrated in FIG. 1.

In use, the operator moves the operating level 33 to the operative position to energize the permanent magnet means 30. The start button 90 is then depressed, and the fluid cylinder 77 operates to move the movable slide plate 39 forward or to the left, as viewed in FIGS. 1 and 4, to bring the holding means steel plate 68 into the dotted line position shown in FIG. 1 against the magnetic means plate 32. When the holding means plate 68 engages the permanent magnet means face plate 32, the fluid cylinder 77 is reversed by the action of the switch operating tab 94 engaging the proximity switch 95. The operating of the switch 95 then reverses the action of the fluid cylinder 77 so as to move its cylinder rod back to the position shown in FIG. 1 and retract the drive plate 80. The operator then mounts seat belt on the holding fixture and inserts the end through the retainer means to have the check roller 20 retain a belt 16 in a position as illustrated in FIG. 1.

It will be seen that the forward movement of the movable slide plate 39 from the solid line position shown in FIG. 1 to the broken line position, where it is held in a first position ready for the mounting of a seat belt, stretches the surgical tubing members 115 and provides a rearwardly directed preload on the movable slide plate 39. For example, in one embodiment the surgical tubing members 115 provided a preload of approximately 32 lbs. pull on the movable slide plate 39, whereas the magnetic holding means 30 was capable of holding approximately four times the preload of 32 lbs. so as to provide a safety factor of four times. With the movable slide plate 39 in the broken line position shown in FIG. 1, and with a seat belt 16 attached, the testing machine is then in a position for a test operation on the seat belt 16. The operator then moves the magnetic check operating lever 33 in the proper direction to de-energize the magnetic holding means 30, whereby the preload on the movable slide plate 39 then moves said plate 39 quickly to the right, back to the solid line position shown in FIG. 1. Normally, the movable slide plate 39 stops short of engaging the bumper plate 104 with the shock absorber 107, and the shock absorber 107 is merely a safety means to stop the slide plate 39 in case it is moved by the tubing members 115 further than its normal movement due to a faulty seat belt retractor. If the seat belt retractor is working properly, it will stop the slide plate 39 within a couple of inches rearward travel, or travel to the right as viewed in FIG. 1, from the broken line position where it is engaged by the magnetic holding means 30. The operator can notice the rearward movement of the indicator 98 along the scale 100 for taking test readings on the seat belt retractor being tested. After the movement of the movable slide plate 39 to the right, the operator again presses the start switch 90 to move the movable slide plate 39 back to the left, as viewed in FIG. 1, to the broken line holding position to permit the operator to remove the first seat belt and retractor that was tested and mounted a second seat belt and retractor for a test thereon.

It will be seen that the static free magnetic holding and release means of the present invention permits the releasing of the movable slide table 39 without any drag or friction which might produce injurious vibrations and noises and other unwanted effects in the test machine. The static free magnetic holding and release means of the present invention is also efficient, safe and fast in operation, in both the securing and releasing actions.

While it will be apparent that the preferred embodiment of the invention herein disclosed is well calculated to fulfill the objects above stated, it will be appreciated that the invention is susceptible to modification, variation and change.

What I claim is:

1. In a static free magnetic holding and release means, the combination of:
   a. a permanent magnet means operable between an energized condition and a de-energized condition;
   b. a preloaded holding means movable to a first position in engagement with said permanent magnet means for a holding engagement with the permanent magnetic means when it is in an energized condition, and movable to a second position by the preload thereon when the permanent magnet means is in a de-energized condition for releasing the holding means;
   c. preload means for imparting a preload in one direction on the holding means to move it to said second position when the permanent magnet is in a de-energized condition, and,
   d. said preloaded holding means including a steel plate engageably by said permanent magnet means, and an aluminum plate secured to the steel plate for operative connection to said preload means.

2. A static free magnetic holding and release means as defined in claim 1, wherein:
   a. said holding means steel plate is attached to said holding means aluminum plate by a free floating attachment means for movement of said two plates relative to each other.

3. A static free magnetic holding and release means as defined in claim 2, wherein said free floating attachment means comprises;
   a. shoulder screw means for attaching the aluminum plate to the steel plate to allow movement of the plates relative to each other; and,
   b. a spring means mounted between said steel plate and said aluminum plate for normally biasing said plates apart.

4. In a seat belt testing machine, the combination comprising:
   a. a support table;
   b. a static free permanent magnet holding and release means mounted on said support table and operable between an energized holding condition and a de-energized release condition;
   c. a movable slide plate movably supported on said table for carrying a seat belt retractor secured thereto;
   d. retainer means adjacent the holding and release means for releasably retaining the free end of a seat belt mounted on the retractor on the movable slide plate;
   e. preload means for imparting a preload in one direction on the movable slide plate to move it to a retracted position; and,
   f. a power means for moving the movable slide plate to an advanced position in holding engagement with the magnetic holding and release means, when it is in a holding condition, against the bias of the preload means, whereby when the permanent magnet means is changed to the release condition the slide plate is retracted by the preload means to impart a test pull on said seat belt and retractor.

5. A seat belt testing machine as defined in claim 4, wherein:
 a. said slide plat is provided with a holding plate means for holding engagement with the permanent magnet holding means.

6. A seat belt testing machine as defined in claim 5, wherein:
 a. said holding plate means includes a steel plate for engagement by said permanent magnet means, and an aluminum plate interconnected between the steel plate and the slide plate.

7. A seat plate testing machine as defined in claim 6, wherein:
 a. said holding means steel plate is attached to said holding means aluminum plate by a free floating attachment means for movement of said two plates relative to each other.

8. A seat belt testing machine as defined in claim 7, wherein said free floating attachment means comprises:
 a. shoulder screw means for attaching the aluminum plate to the steel plate to allow movement of the plates relative to each other; and,
 b. a spring means mounted between said steel plate and said aluminum plate for normally biasing said plates apart.

* * * * *